United States Patent
Morimoto

(10) Patent No.: US 9,947,519 B2
(45) Date of Patent: Apr. 17, 2018

(54) COMPUTATIONAL METHOD AND SYSTEM FOR DEDUCING SUGAR CHAINS USING TANDEM MS$^n$ SPECTROMETRY DATA

(71) Applicant: Shimadzu Corporation, Kyoto-shi, Kyoto (JP)

(72) Inventor: Kentaro Morimoto, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 884 days.

(21) Appl. No.: 14/167,627

(22) Filed: Jan. 29, 2014

(65) Prior Publication Data

US 2014/0249765 A1    Sep. 4, 2014

(30) Foreign Application Priority Data

Mar. 1, 2013  (JP) ................................ 2013-040523

(51) Int. Cl.
*G01N 33/00* (2006.01)
*H01J 49/00* (2006.01)
(Continued)

(52) U.S. Cl.
CPC .......... *H01J 49/0036* (2013.01); *G01N 33/66* (2013.01); *G01N 33/6851* (2013.01); *G06F 19/24* (2013.01); *G01N 2400/10* (2013.01)

(58) Field of Classification Search
CPC .......... G01N 33/5038; G01N 2400/10; G01N 33/6848; G01N 33/6851; H01J 49/0036; G06F 19/24; G06F 19/70
See application file for complete search history.

(56) References Cited

U.S. PATENT DOCUMENTS

| 5,538,897 A * | 7/1996 | Yates, III ................. C07K 1/00 436/173 |
| 2002/0102610 A1* | 8/2002 | Townsend .......... G01N 33/6818 435/7.1 |
| 2004/0111228 A1* | 6/2004 | Kobayashi .......... H01J 49/0036 702/81 |

FOREIGN PATENT DOCUMENTS

| JP | 2005-265697 A | 9/2005 |
| JP | 2008175793 A | 7/2008 |

(Continued)

OTHER PUBLICATIONS

"Mascot Search", [online], Matric Science Ltd., UK [searched on Jun. 20, 2012], 1 page.
(Continued)

*Primary Examiner* — Yelena G Gakh
(74) *Attorney, Agent, or Firm* — Sughrue Mion, PLLC

(57) ABSTRACT

Based on the m/z of a precursor ion used in an MS$^2$ analysis of a test sugar chain, a plurality of sugar-chain structure candidates are extracted from a sugar-chain database in which various sugar-chain structures are related to m/z (S2). Product ions that can be generated by cutting one sugar-chain bond are calculated for each sugar-chain structure candidate (S3). For each combination of two sugar-chain structure candidates, the product ions of one candidate are compared with those of the other to extract characteristic product ions for each sugar-chain structure candidate, and their m/z values are calculated (S4). Whether or not an MS$^2$ spectrum of the test sugar chain has a peak located at m/z of any of the characteristic product ions is determined, and based on the determination result, the sugar-chain structure candidates are narrowed down (S5) and the obtained result is shown on a display unit (S6).

10 Claims, 6 Drawing Sheets

(51) Int. Cl.
    *G01N 33/66*     (2006.01)
    *G01N 33/68*     (2006.01)
    *G06F 19/24*     (2011.01)

(56) References Cited

FOREIGN PATENT DOCUMENTS

| | | |
|---|---|---|
| JP | 2010-133707 A | 6/2010 |
| JP | 2011220733 A | 11/2011 |
| WO | 2012104956 A1 | 8/2012 |

OTHER PUBLICATIONS

Shusaku Daikoku, et al., "Analysis of a series of isomeric oligosaccharides by energy-resolved mass spectrometry: a challenge on homobranched trisaccharides", Rapid Communications in Mass Spectrometry, 2009, pp. 3713-3719, vol. 23.

Akihiko Kameyama, et al., "A Strategy for Identification of Oligosaccharide Structures Using Observational Multistage Mass Spectral Library", Anal. Chem., 2005, pp. 4719-4725, vol. 77.

Communication dated Apr. 26, 2016, from the Japanese Patent Office in counterpart application No. 2013-040523.

* cited by examiner

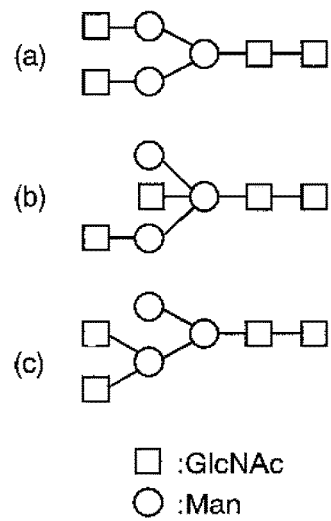
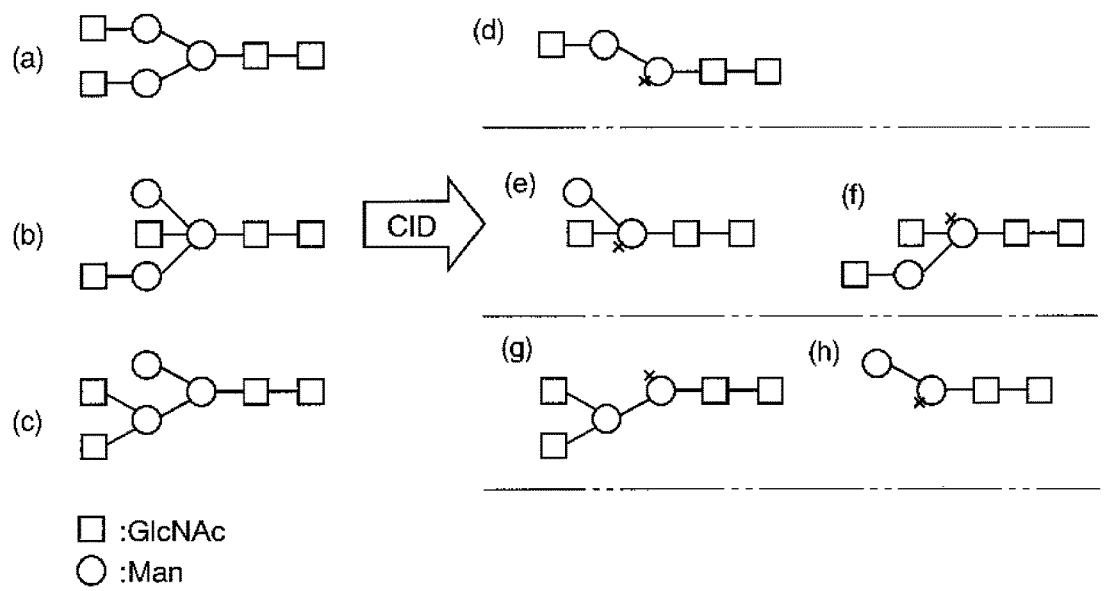

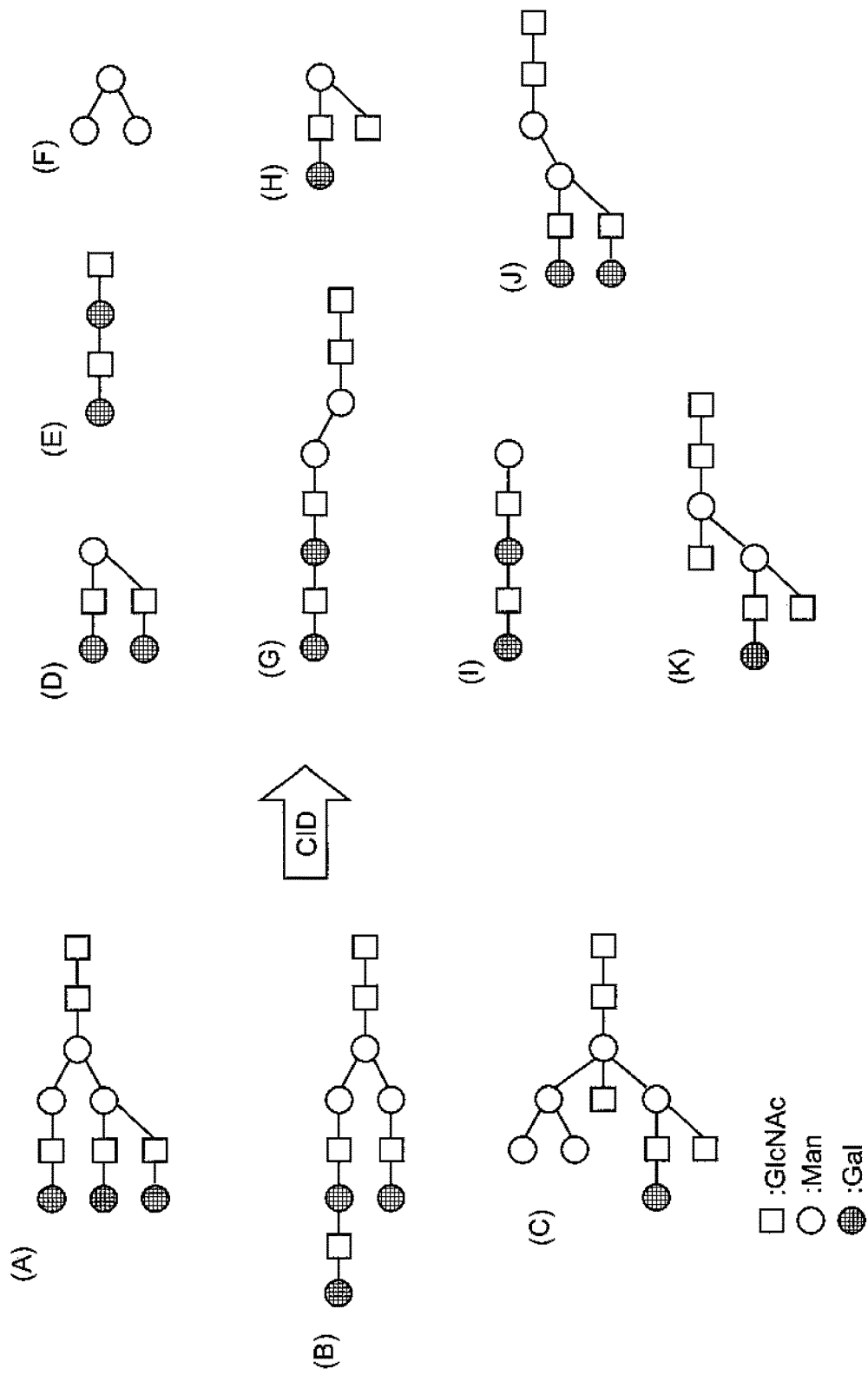

☐ :GlcNAc
◯ :Man

COMPUTATIONAL METHOD AND SYSTEM FOR DEDUCING SUGAR CHAINS USING TANDEM MS$^n$ SPECTROMETRY DATA

TECHNICAL FIELD

The present invention relates to a method and system for analyzing a sugar-chain structure for deducing the structure of a sugar chain by using mass spectrometry.

BACKGROUND ART

In recent years, mass spectrometers have been indispensable for identification and structural analysis of a biological sample containing proteins, sugar chains, lipids or the like. In particular, the technique of MS$^n$ analysis is extremely useful for the structural of proteins, sugar chains or the like. In an MS$^n$ analysis, an ion originating from a sample and having a comparatively large molecular weight is dissociated one or more times by collision induced dissociation (CID) and subjected to mass spectrometry.

A well-known technique for analyzing proteins (or peptides) using a mass spectrometer is a database search method, in which mass-to-charge ratios of the peaks on an MS$^n$ spectrum obtained by an MS$^n$ analysis of a sample are compared with those of the product ions calculated from proteins registered in a database, and the amino acid sequence of a peptide corresponding to the actual measurement data is deduced based on the degree of matching of the mass-to-charge ratios. The "Mascot MS/MS ion search", an online system offered by Matrix Science Ltd, UK, is one of the current and most widely used database search techniques (see Non-Patent Document 1).

On the other hand, as a technique for analyzing a sugar-chain structure using a mass spectrometer, a library search is commonly known, in which an MS$^n$ spectrum pattern obtained by an MS$^n$ analysis of an unknown sample is compared with each of the MS$^n$ spectra stored in a spectrum library in which MS$^n$ spectra obtained by MS$^n$ analyses of samples having known structures are registered, and the sugar-chain structure corresponding to the measurement data is deduced based on the degree of matching of the spectrums (see Non-Patent Document 2). This library search for sugar chain structural analysis differs from the previously described MS/MS ion search aimed at identification of proteins and peptides in that it uses a spectrum library including MS$^n$ spectra of sugar chains having known structures in place of a database including structural information of proteins and other kinds of information, although the spectrum library is also a database in the broad sense.

That is to say, although a difference exists in that the target is an amino acid sequence in case of the MS/MS ion search and a sugar-chain structure in the case of the sugar-chain library search, both methods can be categorized as a technique for identifying a sample by using a database. In these techniques, a substance contained in a sample is identified by comparing an actually measured mass spectrum to be identified with theoretical fragment information of peptides obtained from a database or mass spectra obtained by actual measurements of sugar chains. The eventually presented result is selected based on the degree of matching evaluated in the process of comparison.

The reason why the MS/MS ion search is effective for the identification and structural analysis of peptides is because, even if there are different kinds of peptides whose amino acid sequences partially include the same sequence pattern, the theoretical calculation of the mass-to-charge ratios of the product ions will, in many cases, reveal a unique combination of mass-to-charge ratio values of the product ions for each peptide. However, the MS/MS ion search or similar analytical techniques are not very effective for sugar-chain structural analysis. This is because sugar chains are extremely varied in structure and can take a variety of forms with the same mass and composition. Sugar chains having different structures and yet being identical in composition generate a number of product ions with the same combination of mass-to-charge ratios. Therefore, it is impossible to determine the structure of a sugar chain by merely evaluating the degree of matching of the mass-to-charge ratios of the product ions. This is the reason the technique of comparing MS$^n$ spectra by library search is used in the sugar-chain analysis.

In a commonly used, conventional sugar-chain library search, the sugar-chain structure of an unknown sample is deduced by comparing an MS$^n$ spectrum of the sample with MS$^n$ spectra registered in a spectrum library in terms of not only the values of the mass-to-charge ratios of the peaks on the MS$^n$ spectra but also the signal intensity information contained in the MS$^n$ spectra. Comparing not only the mass-to-charge-ratio values of the peaks on MS$^n$ spectra but also their signal intensity values makes it possible to additionally identify structural isomers, such as positional or anomeric isomers. For example, Non-Patent Document 2 and Patent Document 1 suggest that the use of signal intensity information contained in MS$^n$ spectra makes it possible to identify a positional isomer in terms of not only which of the carbons in a simple sugar is engaged in the bonding but also whether the bond is an $\alpha$ or $\beta$ bond.

However, in such a sugar-chain library search, if an MS$^n$ spectrum matching the unknown sugar-chain structure of a target sample is not included in the spectrum library, the MS$^n$ spectrum obtained by an actual measurement of the target sample cannot be identified at all or is incorrectly identified as a different kind of sugar chain or structure. To improve identification accuracy, it is necessary to enrich the spectrum library, which is an extremely laborious task and requires an enormous amount of time and labor.

Applying the sugar-chain library search requires satisfying the rigorous constraint that the measurement of unknown samples be performed under the same conditions (such as the sample preparation method, labeling method, and dissociation energy) as used when the MS$^n$ spectra included in the spectrum library were obtained. For example, the library search disclosed in Non-Patent Document 2 requires 2-aminopyridine (PA) labeling a sugar-chain sample and performing a measurement of the sample with a matrix-assisted laser desorption/ionization ion-trap time-of-flight mass spectrometer (MALDI-QIT-TOFMS). The kind of matrix to be used for preparing the sample and the amount of dissociation energy are also limited.

BACKGROUND ART DOCUMENT

Patent Document

Patent Document 1: JP-A 2010-133707

Non-Patent Document

Non-Patent Document 1: "Mascot Search", [online], Matric Science Ltd., UK, [searched on Jun. 20, 2012]
Non-Patent Document 2: S. Daikoku et al, "Analysis of a series of isomeric oligosaccharides by energy-resolved mass spectrometry: a challenge on homobranched trisaccharides", *Rapid Communications in Mass Spectrometry*, Vol. 23 (2009), pp. 3713-3719

SUMMARY OF THE INVENTION

Problem to be Solved by the Invention

The present invention has been developed to solve the previously described problem, and its objective is to provide a method and system for analyzing a sugar-chain structure by which a sugar-chain structure can be deduced with high reliability without requiring a spectrum library including a collection of $MS^n$ spectra obtained by actual measurements of sugar chains having known structures as well as without depending on the sample preparation method or other conditions applied in the $MS^n$ analysis of an unknown sample.

Means for Solving the Problem

The first aspect of the present invention aimed at solving the previously described problem is a sugar-chain analyzing method for deducing the structure of a test sugar chain by using an $MS^2$ spectrum data obtained by performing an $MS^2$ analysis of the test sugar chain, including:

a) a structure candidate obtaining step, in which a plurality of sugar-chain structure candidates of the test sugar chain are obtained based on the mass-to-charge ratio of a precursor ion used in the $MS^2$ analysis of the test sugar chain;

b) a characteristic ion obtaining step, in which product ions that can be generated by dissociation of a sugar-chain structure candidate are calculated for each of the plurality of sugar-chain structure candidates, and a characteristic product ion is extracted from the calculated product ions for each of the sugar-chain structure candidates; and c) a structure candidate judging step, in which a peak having a mass-to-charge ratio of the characteristic product ion is detected in the $MS^2$ spectrum obtained for the test sugar chain, and the degree of reliability of each of the sugar-chain structure candidates is judged based on a result of the detection.

The second aspect of the present invention aimed at solving the previously described problem is a system for carrying out the sugar-chain analyzing method according to the first aspect of the present invention. More specifically, it is a sugar-chain analyzing system for deducing the structure of a test sugar chain by using an $MS^2$ spectrum data obtained by performing an $MS^2$ analysis of the test sugar chain, including:

a) a structure candidate obtaining section for obtaining a plurality of sugar-chain structure candidates of the test sugar chain, based on the mass-to-charge ratio of a precursor ion used in the $MS^2$ analysis of the test sugar chain;

b) a characteristic ion obtaining section for calculating product ions that can be generated by dissociation of each of the plurality of sugar-chain structure candidates, and for extracting a characteristic product ion from the calculated product ions for each of the sugar-chain structure candidates; and c) a structure candidate judging section for detecting a peak having a mass-to-charge ratio of the characteristic product ion in the $MS^2$ spectrum obtained for the test sugar chain, and for judging the degree of reliability of each of the sugar-chain structure candidate based on a result of the detection.

In the sugar-chain structure analyzing method according to the first aspect of the present invention embodied by the sugar-chain structure analyzing system according to the second aspect of the present invention, the structure of a test sugar chain is deduced as follows, based on an $MS^2$ spectrum data obtained by performing an $MS^2$ analysis of a sample containing the test sugar chain: Initially, in the structure candidate obtaining step, a plurality of sugar-chain structure candidates of the test sugar chain are obtained based on the mass-to-charge ratio of the precursor ion used in the $MS^2$ analysis. As stated earlier, in many cases, a number of sugar-chain structure candidates are extracted since sugar chains can take various structures with the same mass and the same composition.

To obtain sugar-chain structure candidates, it is preferable, for example, to use a database in which mass-to-charge ratios of precursor ions originating from sugar chains are stored, with each precursor ion related to a plurality of sugar-chain structures. With the mass-to-charge ratio of the precursor ion used in the $MS^2$ analysis given as information, a list of sugar-chain structure candidates can be created by setting a mass-to-charge-ratio range including the given mass-to-charge ratio with a predetermined margin, and extracting, from the database, sugar-chain structures related to the mass-to-charge ratios included in the aforementioned range. This holds true for the third and fourth aspects of the present invention, which will be described later.

Subsequently, in the characteristic ion obtaining step, theoretical product ions (i.e. the product ions that can be generated by a CID or similar dissociating operation) are calculated for each of the plurality of sugar-chain structure candidates extracted in the previous step. The computation is basically aimed at finding product ions that can be generated by cutting a bond between the sugars constituting the sugar-chain structure by the dissociating operation. However, the number of kinds of product ions will be enormous if the number of bonds that will be cut by one dissociating operation is not fixed. In the case of the CID, it is possible to appropriately adjust the amount of CID energy and other CID conditions so that only one bond will be cut by one dissociating operation. Accordingly, it is preferable to appropriately set CID conditions in the $MS^2$ analysis and perform the computation of product ions in the characteristic ion obtaining step under the condition that only one bond in the sugar-chain structure is cut.

Furthermore, in the characteristic ion obtaining step, a number of product ions obtained for each sugar-chain structure candidate are compared with each other to extract, for each sugar-chain structure candidate, a characteristic product ion with a low degree of commonness to the other sugar-chain structure candidates. The phrase "with a low degree of commonness to the other sugar-chain structure candidates" means that the product ion in question is not common to all the other sugar-chain structure candidates.

Subsequently, in the structure candidate judging step, the mass-to-charge ratios of the characteristic product ions are determined, after which an $MS^2$ spectrum obtained by an actual measurement of the test sugar chain is investigated to determine whether or not an ion peak exists at the mass-to-charge ratio of any of the characteristic product ions. For example, if a characteristic product ion which appears only in one sugar-chain structure candidate and for which there is no other characteristic product ions having the same mass-to-charge ratio is present on the actually measured $MS^2$ spectrum, it is possible to deduce, with high reliability, that the sugar-chain structure candidate concerned is the actual sugar-chain structure. Even if the sugar-chain structure candidates cannot be narrowed down to one, the degree of reliability of each candidate can be determined by checking whether or not a peak exists at the mass-to-charge ratio of any of the characteristic product ions related to that candidate and totalizing the check results, and less reliable candidates can be excluded or the candidates can be ranked according to their degrees of reliability. By presenting such results on a display unit, for example, an analysis operator can obtain information about the structure of the test sugar chain.

In the first and second aspects of the present invention, $MS^2$ spectrum data of a test sugar chain is used as the basis for deducing the structure of the test sugar chain. The sugar-chain structure candidates can be further narrowed down by using a result of an $MS^n$ analysis with n equal to or greater than three.

Thus, the third aspect of the present invention, which is an extended version of the first aspect of the present invention, provides a sugar-chain structure analyzing method for deducing the structure of a test sugar chain by using $MS^n$ spectrum data obtained by performing an $MS^n$ analysis of the test sugar chain (n=2, 3, . . . , where the largest value of n is an integer equal to or greater than three), including:

a) a structure candidate obtaining step, in which a plurality of sugar-chain structure candidates of the test sugar chain are obtained based on the mass-to-charge ratio of a precursor ion used in an $MS^2$ analysis of the test sugar chain;

b) a first characteristic ion obtaining step, in which product ions that can be generated by dissociation of a sugar-chain structure candidate are calculated for each of the plurality of sugar-chain structure candidates, and a characteristic product ion is extracted from the calculated product ions for each of the sugar-chain structure candidates;

c) a characteristic ion detecting step, in which a peak having a mass-to-charge ratio of the characteristic product ion extracted in the first characteristic ion obtaining step or in a second characteristic ion obtaining step to be mentioned later is detected in an $MS^m$ spectrum (m=2, . . . , where the largest value of m is n−1) obtained for the test sugar chain;

d) an $MS^{m+1}$ analyzing step, in which an $MS^{m+1}$ analysis of the test sugar chain is performed, where the mass-to-charge ratio of the characteristic product ion detected in the characteristic ion detecting step is set as the precursor ion;

e) a second characteristic ion obtaining step, in which secondary product ions that can be generated by dissociation of a characteristic product ion having the mass-to-charge ratio of the precursor ion used in the $MS^{m+1}$ analysis is calculated, and a characteristic secondary product ion is extracted from the calculated secondary product ions for each of the characteristic product ions before dissociation; and f) a structure candidate judging step, in which a peak having a mass-to-charge ratio of the characteristic secondary product ion is detected in the $MS^{m+1}$ spectrum obtained for the test sugar chain, a characteristic product ion before dissociation in the final stage of the $MS^{m+1}$ analysis is identified based on a result of the detection, and the degree of reliability of each of the plurality of sugar-chain structure candidates is judged based on a result of the identification as well as a result of the peak detection in the characteristic ion detecting step, wherein, after the structure candidate obtaining step and the first characteristic ion obtaining step are performed, the characteristic ion detecting step, the $MS^{m+1}$ analyzing step and the second characteristic ion obtaining step are performed one or more times while sequentially increasing the value of m from two, and subsequently, the structure candidate judging step is performed to narrow down the sugar-chain structure candidates.

The fourth aspect of the present invention is a system for carrying out the sugar-chain structure analyzing method according to the third aspect of the present invention. More specifically, it is a sugar-chain structure analyzing system for deducing the structure of a test sugar chain by using $MS^n$ spectrum data obtained by performing an $MS^n$ analysis of the test sugar chain (n=2, 3, . . . , where the largest value of n is an integer equal to or greater than three), including:

a) a structure candidate obtaining section for obtaining a plurality of sugar-chain structure candidates of the test sugar chain, based on the mass-to-charge ratio of a precursor ion used in an $MS^2$ analysis of the test sugar chain;

b) a first characteristic ion obtaining section for calculating product ions that can be generated by dissociation of a sugar-chain structure candidate for each of the plurality of sugar-chain structure candidates, and for extracting a characteristic product ion from the calculated product ions for each of the sugar-chain structure candidates;

c) a characteristic ion detecting section for detecting, in an $MS^m$ spectrum (m=2, . . . , where the largest value of m is n−1) obtained for the test sugar chain, a peak having a mass-to-charge ratio of the characteristic product ion extracted by the first characteristic ion obtaining section or by a second characteristic ion obtaining section to be mentioned later;

d) an $MS^{m+1}$ analyzing section for performing an $MS^{m+1}$ analysis of the test sugar chain, where the mass-to-charge ratio of the characteristic product ion detected by the characteristic ion detecting section is set as the precursor ion;

e) a second characteristic ion obtaining section for calculating secondary product ions that can be generated by dissociation of a characteristic product ion having the mass-to-charge ratio of the precursor ion used in the $MS^{m+1}$ analysis, and for extracting a characteristic secondary product ion from the calculated secondary product ions for each of the characteristic product ions before dissociation; and f) a structure candidate judging section for detecting a peak having a mass-to-charge ratio of the characteristic secondary product ion in the $MS^{m+1}$ spectrum obtained for the test sugar chain, for identifying a characteristic product ion before dissociation in the final stage of the $MS^{m+1}$ analysis based on the result of the detection, and for judging the degree of reliability of each of the plurality of sugar-chain structure candidates based on the result of the identification as well as the result of the peak detection by the characteristic ion detecting section, wherein, after the processes by the structure candidate obtaining section and the first characteristic ion obtaining section are performed, the processes by the characteristic ion detecting section, the $MS^{m+1}$ analyzing section and the second characteristic ion obtaining section are performed one or more times while sequentially increasing the value of m from two, and subsequently, the process by the structure candidate judging section is performed to narrow down the sugar-chain structure candidates.

In the case where a product ion characteristic of a first sugar-chain structure candidate and a product ion characteristic of a second sugar-chain structure candidate has the same mass-to-charge ratio, even if an ion peak corresponding to that mass-to-charge ratio has been located in the actually measured $MS^m$ spectrum, it is impossible to determine which of the first and second sugar-chain structure candidates is the actual structure of the test sugar chain. In such a case, it is preferable to perform an $MS^{m+1}$ analysis in which the mass-to-charge ratio of a peak of an ion located in the actually measured $MS^m$ spectrum (a characteristic product ion having an undetermined structure) is set as the precursor ion. The possibility exists that the structure of the precursor ion can be determined by checking whether or not a product ion that can be expected from the undetermined structure of the precursor ion is present on the obtained $MS^{m+1}$ spectrum.

Accordingly, in the third and fourth aspects of the present invention, the dissociating operation is repeated two or more times to determine the structure of a characteristic product ion having an undetermined structure in a stepwise manner, whereby the sugar-chain structure candidates can eventually be narrowed down to one or a small number.

Effect of the Invention

With the method and system for analyzing a sugar-chain structure according to the present invention, a sugar-chain structure is deduced without using a spectrum library including the results obtained by actual $MS^n$ analyses of sugar chains having known structures. Therefore, even the structure of a sugar chain not included in the library can be deduced with high reliability. The efficiency of analyzing work will also be improved, since the task of enriching the library is unnecessary. Furthermore, in the method and system for analyzing a sugar-chain structure according to the present invention, there is virtually no limitation on the sample preparation method and the type of device to be used for an $MS^n$ analysis of a test sugar chain, since it is unnecessary to evaluate the degree of matching of a target spectrum or other kinds of information with the measurement results included in the library created by using a specific sample preparation method and a specific type of device. Accordingly, the time and labor for sample preparation can be omitted. The degree of freedom of the measurement will also be improved.

BRIEF DESCRIPTION OF THE DRAWINGS

FIG. 3 is a model diagram showing a specific example of the procedure of deducing a sugar-chain structure according to the first embodiment.

FIG. 4 is a model diagram showing a specific example of the procedure of deducing a sugar-chain structure according to the first embodiment.

FIG. 5 is a model diagram showing another specific example of the procedure of deducing a sugar-chain structure according to the first embodiment.

MODE FOR CARRYING OUT THE INVENTION

[First Embodiment]

Figure 1:
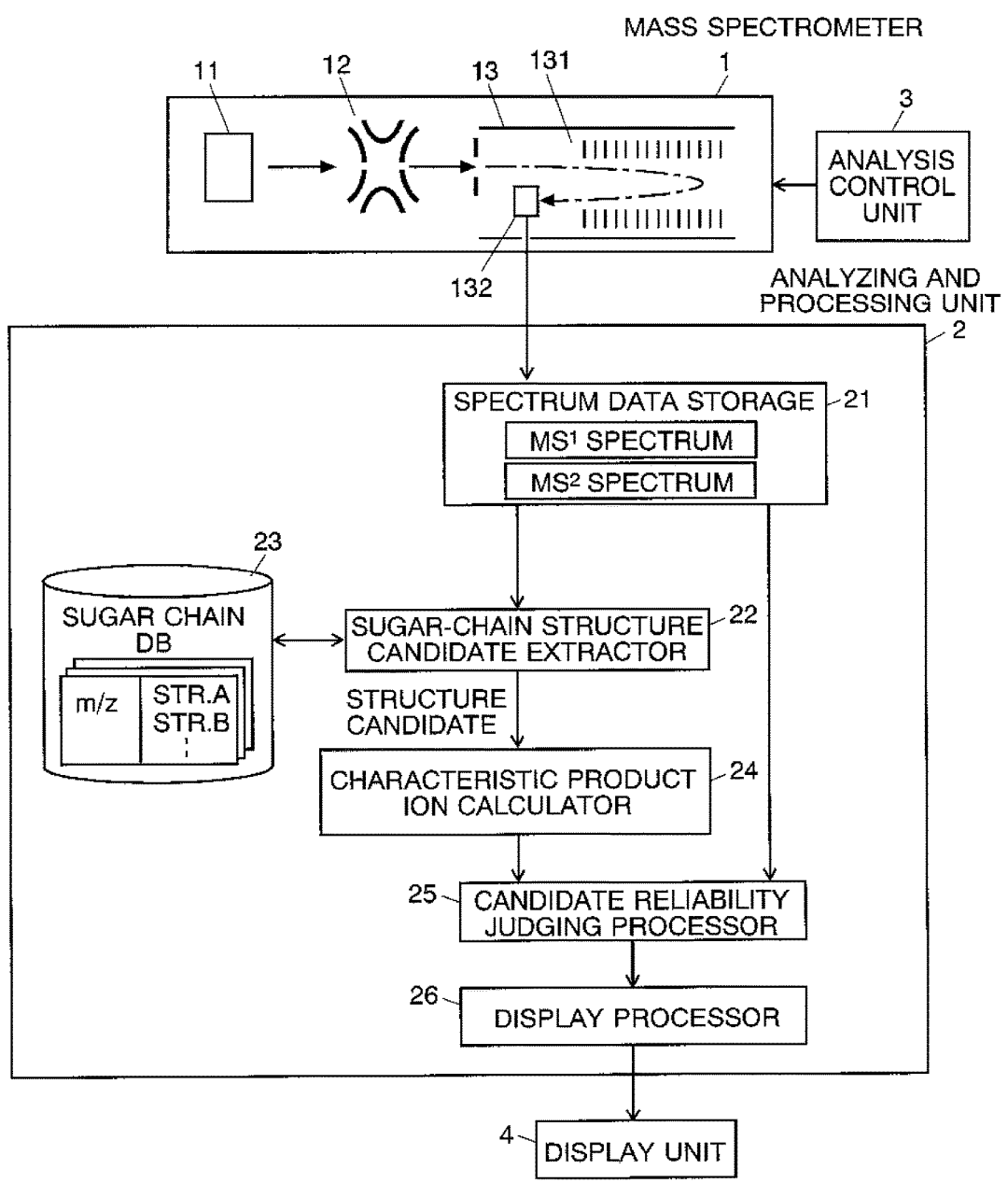
FIG. 1 is a schematic configuration diagram of a sugar-chain structure analyzing system as the first embodiment of the present invention.

A sugar-chain structure analyzing system as one embodiment (first embodiment) of the present invention is hereinafter described with reference to the attached drawings. FIG. 1 is an overall configuration diagram of the sugar-chain structure analyzing system of the present embodiment.

The sugar-chain structure analyzing system of the present embodiment is composed of three major sections: a mass spectrometer 1, an analyzing and processing unit 2 (which mainly consists of a computer), and an analysis control unit 3. In the present example, the mass spectrometer 1 is a matrix-assisted laser desorption/ionization ion-trap time-of-flight mass spectrometer (MALDI-IT-TOFMS), which includes: a MALDI ion source 11 for ionizing molecules or atoms in a sample to be analyzed; a three-dimensional quadrupole ion trap 12 capable of temporarily capturing the ions generated by the ion source 11, selecting specific ions according to their mass-to-charge ratio and performing an ion-dissociating operation by collision induced dissociation (CID); and a time-of-flight mass spectrometer 13 for receiving various ions collectively ejected from the ion trap 12 and for detecting the ions after separating them according to their mass-to-charge ratios. The time-of-flight mass spectrometer 13 includes a reflectron-type flight space 131 in which ions are made to reverse their direction due to the effect of a direct-current electric field created by a reflector and a detector 132 for sequentially detecting ions which have been separated during their flight through the flight space 131.

The analyzing and processing unit 2 includes the following functional blocks: a spectrum data storage 21 for digitizing and storing detection signals from the detector 132 at predetermined intervals of time; a sugar-chain database (DB) 23 in which each of various sugar chains are related to the mass-to-charge ratio and its various possible structures; a sugar-chain structure candidate extractor 22 for extracting candidates of the sugar-chain structure for a sample subjected to a measurement, using the sugar-chain DB 23; a characteristic product ion calculator 24 for deducing, for each of the sugar-chain structure candidates, product ions which will be generated when the sugar-chain structure candidate is dissociated by CID, and for finding, for each of the sugar-chain structure candidates, a characteristic product ion which is unique to the candidate in question or which has a low degree of commonness; a candidate reliability judging processor 25 for ranking the sugar-chain structure candidates or selecting one or more of them according to their degrees of reliability, based on the calculation result of the characteristic product ion and the actually measured $MS^2$ spectrum; and a display processor 26 for presenting an analysis result showing the ranked or selected sugar-chain structure candidates on a display unit 4. The analyzing and processing unit 2 and the analysis control unit 3 can be realized by using a personal computer provided as hardware resources and executing a dedicated controlling and processing software program previously installed on the computer.

Figure 2:
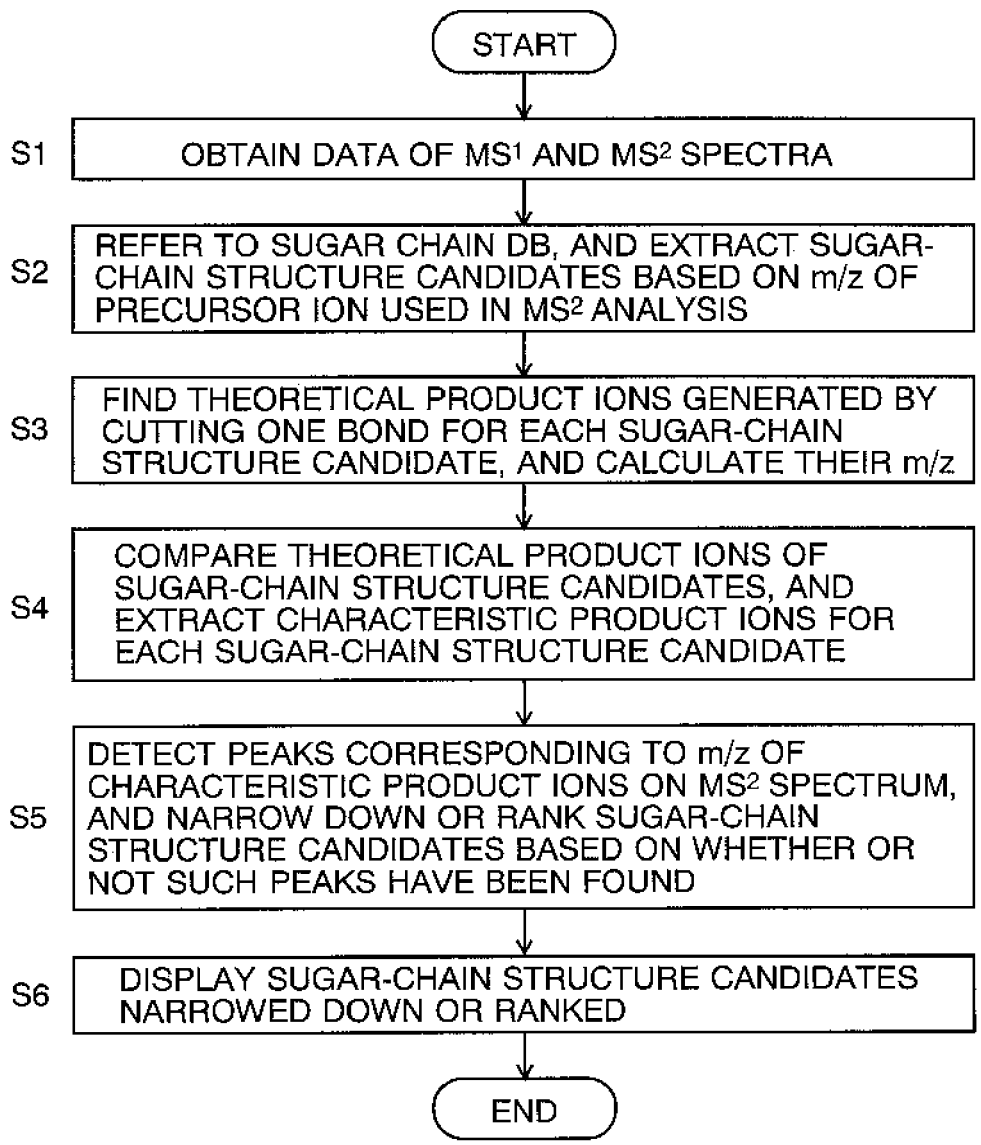
FIG. 2 is a flowchart showing a procedure of the sugar-chain structure analysis performed by the sugar-chain structure analyzing system of the first embodiment.

One example of the data analyzing process for identifying the structure of a test sugar chain in a sample in the sugar-chain structure analyzing system of the present embodiment, is hereinafter described with reference to the flowchart shown in FIG. 2. FIGS. 3-5 are model diagrams showing a specific example of the present sugar-chain structure deduction process.

Initially, in the mass spectrometer 1 under the control by the analysis control unit 3, a sample containing a test sugar chain is subjected to an $MS^1$ analysis with no CID operation performed by the ion trap 12 and an $MS^2$ analysis with a CID operation using an ion originating from the test sugar chain as the precursor ion, to collect data of $MS^1$ and $MS^2$ spectra, respectively (Step S1). Those data are temporarily stored in the spectrum data storage 21. In the MS² analysis, the CID conditions in the ion trap 12 should be appropriately set so that the sugar chain is cut in only one bond (not in two or more bonds). This is essential because the sugar-chain structure deduction (to be described later) is performed on the assumption that the sugar chain is cut in only one bond in one CID operation. The CID conditions include CID energy (specifically, the voltage for exciting ions), CID gas pressure, CID gas species and so on. Normally, it is possible to make a sugar chain cut in only one bond by appropriately controlling the CID energy. It is naturally possible to perform noise removal, centroiding or other kinds of appropriate data processing on the data obtained with the mass spectrometer 1.

After the MS¹ and MS² spectra data of the test sugar chain are collected in the previously described manner, the sugar-chain structure candidate extractor 22 obtains mass-to-charge-ratio information of the precursor ion used in the MS² analysis and sets a mass-to-charge-ratio range including the obtained mass-to-charge ratio with a predetermined margin assigned to it. For example, the range may be defined as $M-\Delta M$ to $M+\Delta M$, where $M$ is the value of the mass-to-charge ratio and $\pm\Delta M$ is the margin. Then, the sugar-chain structure candidate extractor 22 accesses the sugar-chain database 23 and extracts, as the sugar-chain structure candidates, all the sugar-chain structures included in that mass-to-charge-ratio range (Step S2).

A sugar chain is composed of a plurality of sugars (simple sugars). For the sugars, there are only a limited number of choices, such as glucose, mannose and galactose. Therefore, the composition of the sugar chain, i.e. the kinds and numbers of the sugars, can be easily determined if the mass-to-charge ratio of a precursor ion originating from the sugar chain. For example, if the mass-to-charge ratio of the precursor ion is 1298 Da and the margin is 2 Da, the sugar-chain composition will be calculated as three mannoses (Man) and four N-acetyl-D glucosamine (GlcNAc). In this case, the sugar-chain structures which can be taken by an N-type sugar chain derived from the sugar-chain database 23 are the three kinds of structures (a), (b) and (c) shown in FIG. 3. These are the sugar-chain candidate structures.

Next, the characteristic product ion calculator 24 calculates the mass-to-charge ratios of theoretical product ions for each sugar-chain structure candidate (Step S3), and determines the mass-to-charge ratio of a characteristic product ion available for narrowing down the sugar-chain structure candidates (Step S4). A characteristic product ion can generally be defined as a product ion that is not common to all the sugar-chain structure candidates. In the present embodiment, it is more strictly defined as a product ion that is present in the sugar-chain structure candidate concerned but cannot be found in any other candidates.

One specific method for calculating the mass-to-charge ratio of such a characteristic product ion is as follows: Initially, for each sugar-chain structure candidate, the mass-to-charge ratios of product ions that can be generated by cutting any one sugar-chain bond (side) are calculated and listed, allowing a redundant occurrence of the same value. If n candidates of the sugar chain have been found, the lists are compared with each other for each of the $_nC_2$ combinations of the candidates, and the mass-to-charge ratios of the product ions that are common to the two lists are deleted, leaving only the mass-to-charge ratios of the product ions which occur only in one of the two lists. The mass-to-charge ratios remaining in the end in each list are adopted as the calculation result of the mass-to-charge ratios of the characteristic product ions of the corresponding sugar-chain structure candidate.

FIG. 4 shows the structures of characteristic product ions respectively calculated for the three kinds of sugar-chain structure candidates (a), (b) and (c) shown in FIG. 3. In the case where only one of the sugar-chain bonds is cut by CID, the calculation result will be the five kinds of characteristic product ions (d)-(h) shown in FIG. 4.

In FIG. 4, (d) is a product ion that can only be obtained from candidate (a), and (e) is a product ion that can only be obtained from candidate (b). Both product ions have the same mass-to-charge ratio and are composed of two Man and three GlcNAc. Such a product ion with a mass-to-charge ratio corresponding to two Man and three GlcNAc cannot be generated by dissociating any bond in the structure of candidate (c). Product ion (f) is only obtained from candidate (b), while product ion (g) is only obtained from candidate (c). These two ions have the same mass-to-charge ratio and are composed of two Man and four GlcNAc. Such a product ion with a mass-to-charge ratio corresponding to two Man and four GlcNAc cannot be generated by dissociating any bond in the structure of candidate (a). Product ion (h) is only obtained from candidate (c). Its mass-to-charge ratio corresponds to two Man and two GlcNAc. A product ion with this mass-to-charge ratio cannot be generated by dissociating any bond in the structure of candidate (a) or (b).

After the mass-to-charge ratios of the characteristic product ions are calculated for each sugar-chain structure candidate, the candidate reliability judging processor 25 retrieves an actually obtained MS² spectrum from the spectrum data storage 21, determines whether or not the MS² spectrum has a peak located at a position corresponding to the mass-to-charge ratio of any of the aforementioned characteristic product ions, and based on the determination result, narrows down the sugar-chain structure candidates or determines their ranking (Step S5).

For example, in the case of FIG. 4, if a peak having the mass-to-charge ratio of product ion (h) (i.e. a mass-to-charge ratio corresponding to two Man and two GlcNAc) has been found on the MS² spectrum, the sugar-chain structure can be narrowed down to candidate (c) and thus uniquely identified. If a peak having the mass-to-charge ratio of product ion (d) or (e) (i.e. a mass-to-charge ratio corresponding to two Man and three GlcNAc) has been found on the MS² spectrum, candidate (c) can be removed since the peak cannot originate from this candidate. If a peak having the mass-to-charge ratio of product ion (f) or (g) (i.e. a mass-to-charge ratio corresponding to two Man and four GlcNAc) has been found on the MS² spectrum, candidate (a) can be removed since the peak cannot originate from this candidate. In these two cases, the candidates cannot be narrowed down to one but can be decreased to a smaller number.

In these two cases, the two remaining candidates have the same degree of reliability. In the case of a sugar chain having a more complex structure, the mass-to-charge ratios of a larger number of characteristic product ions will be calculated from each sugar-chain structure candidate. In such a case, it is possible to count the peaks corresponding to the characteristic product ions on the MS² spectrum and determine the ranking of the sugar-chain structure candidates according to the number of peaks.

The display processor 26 shows, as an analysis result, the narrowed down or ranked sugar-chain structure candidates on the screen of the display unit 4 (Step S6). Thus, the analysis operator can obtain information relating to the structure of the test sugar chain.

FIG. 5 is a model diagram showing another specific example of deducing a sugar-chain structure by the sugar-chain structure analyzing system of the first embodiment.

prepared as in Table 1. In this table, for each sugar-chain structure candidate, the white circles (o) indicate the product ions which should be detected for that candidate, while the crosses (x) indicate the product ions which should not be detected.

TABLE 1

| | Group | | | | | | | |
|---|---|---|---|---|---|---|---|---|
| | Group 1 (m1) | | Group 2 (m2) | | Group 3 (m3) | | Group 4 (m4) | Group 5 (m5) |
| Candidate | D (m1) | I [m1] | G [m2] | J [m2] | E [m3] | H [m3] | F [m4] | K [m5] |
| A | o | x | x | o | x | x | x | x |
| B | x | o | o | x | o | x | x | x |
| C | x | x | x | x | x | o | o | o |

In the case of a precursor ion having a mass-to-charge ratio of 2106.8 Da, the N-type sugar-chain structure candidates that can be obtained from the sugar-chain database 23 are the three structures (A), (B) and (C) shown in FIG. 5. Since Man and Gal have the same mass-to-charge ratio and cannot be distinguished by their compositions, what can be said at this stage is that (A) and (B) differ from (C) in composition. A calculation from those sugar-chain structure candidates shows that there are the eight kinds of characteristic product ions (D)-(K). The "parent-child" relationship between a precursor ion and product ions generated by cutting one bond in the sugar-chain of the precursor ion is as follows:

$$-(A) \rightarrow (D[m1]) \text{ and } (J[m2])$$

$$-(B) \rightarrow (E[m3]), (G[m2]) \text{ and } (I[m1])$$

$$-(C) \rightarrow (F[m4]), (H[m3]) \text{ and } (K[m5])$$

where the codes in the brackets [ ] indicate the mass-to-charge ratios of the respective product ions, with the same code representing the same mass-to-charge ratio.

Grouping the product ions by their mass-to-charge ratios results in five groups: <(D[m1], (I[m1])> with a mass-to-charge ratio of m1, <(G[m2], (J[m2])> with a mass-to-charge ratio of m2, <(E[m3], (H[m3])> with a mass-to-charge ratio of m3, <(F[m4])> with a mass-to-charge ratio of m4, and <(K[m5])> with a mass-to-charge ratio of m 5. If the product ion or ions belonging to one group are not commonly associated with two or more sugar-chain structure candidates, the sugar-chain structure candidates can be narrowed down to one. Accordingly, it is possible to derive the following conclusions as to what kinds of product ions should be present or absent for each sugar-chain structure candidate:

If the actual sugar-chain structure is (C), (F[m4]) and (K[m5]) should appear as the characteristic product ions.

If the actual sugar-chain structure is (B), (F[m4]) and (K[m5]) should not appear, and (E[m3]), (I[m1]) and (G[m2]) should appear as the characteristic product ions.

If the actual sugar-chain structure is (A), (F[m4]), (K[m5]) and (E[m3]) should not appear, and (D[m1]) and (J[m2]) should appear as the characteristic product ions.

To assist in the understanding of the previous explanation, a table showing what combination of product ions will be detected from each sugar-chain structure candidate has been As is evident from Table 1, although the group of product-ions calculated from each of the sugar-chain structure candidates includes (different kinds of) product ions having the same mass-to-charge ratio, the sugar-chain structure candidates can be distinguished from each other when product ions having different mass-to-charge ratios are detected between them. Thus, by extracting characteristic product ions that can be created by a single CID operation for each sugar-chain structure candidate and determining whether or not the peaks corresponding to the mass-to-charge ratios of those product ions are present on an $MS^2$ spectrum obtained by an actual measurement, it is possible to determine the sugar-chain structure. That is to say:

If ions of Group 4 (m4) and Group 5 (m5) have been detected, the sugar-chain structure is (C).

If ions of Group 1 (m1) and Group 2 (m2) have been detected (which is also the case with the sugar-chain structure (A)), and furthermore, if an ion of Group 3 (m3) has also been detected, the sugar-chain structure is (B).

If ions of Group 1 (m1) and Group 2 (m2) have been detected (which is also the case with the sugar-chain structure (B)), and furthermore, if no ion of Group 3 (m3) has been detected, the sugar-chain structure is (A).

[Second Embodiment]

Figure 6:
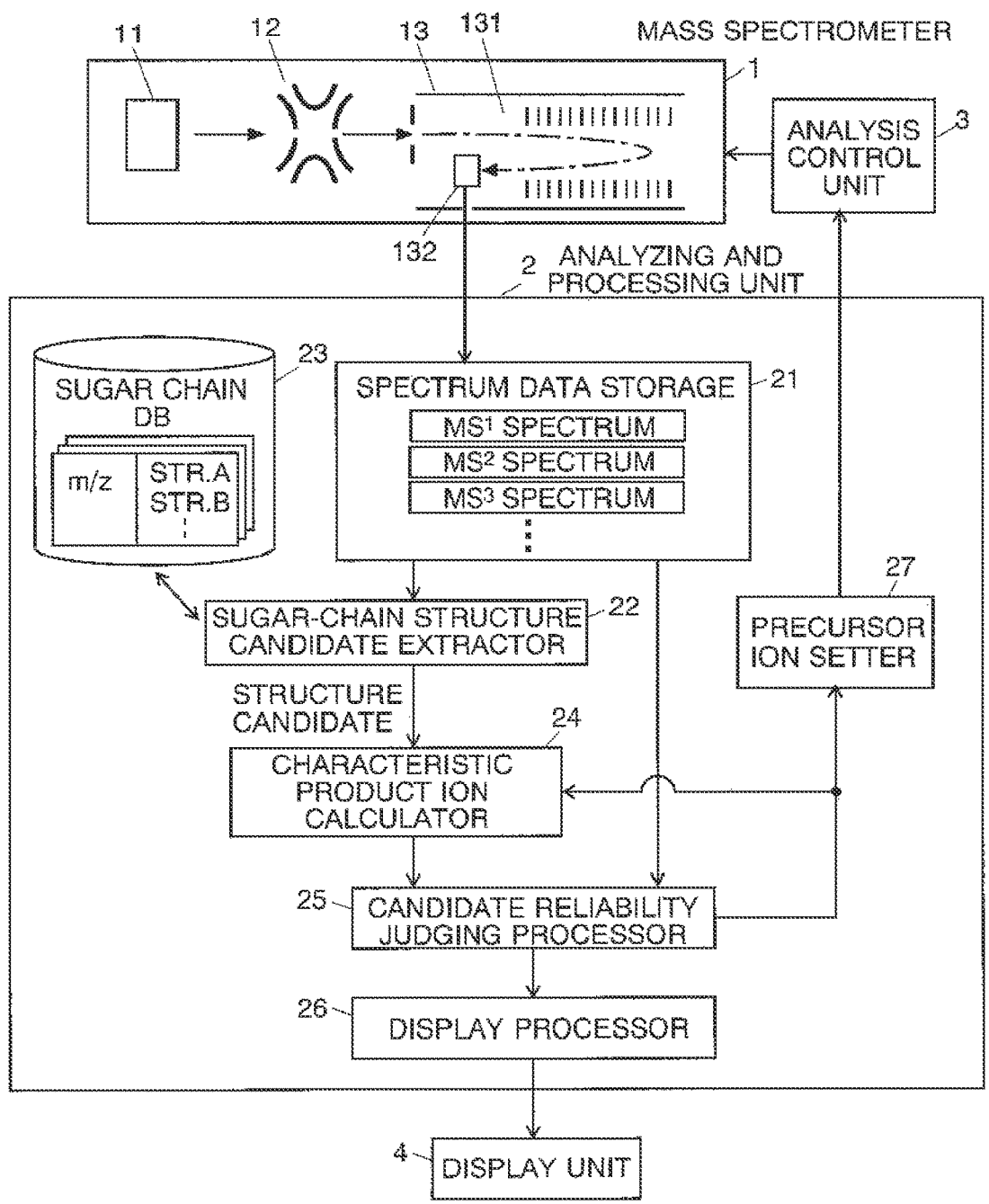
FIG. 6 is a schematic configuration diagram of a sugar-chain structure analyzing system as the second embodiment of the present invention.

A sugar-chain structure analyzing system as another embodiment (second embodiment) of the present invention is hereinafter described with reference to FIGS. 6-8. FIG. 6 is an overall configuration diagram of the sugar-chain structure analyzing system of the present embodiment, where the components identical or corresponding to those used in the system configuration of the first embodiment shown in FIG. 1 are denoted by the same numerals. In the sugar-chain structure analyzing system of the first embodiment, the mass spectrometer 1 performs up to an $MS^2$ analysis. By contrast, in the second embodiment, the mass spectrometer 1 performs an $MS^n$ analysis with n being equal to or greater than three. The precursor ion for the $MS^n$ analysis with n being equal to or greater than three is set by a precursor ion setter 27 based on the result provided from the candidate reliability judging processor 25. The result obtained by the candidate reliability judging processor 25 is also sent to the characteristic product ion calculator 24. In addition to the calculation of the characteristic product ions based on the $MS^2$ analysis, the characteristic product ion calculator 24 calculates characteristic product ions based on the $MS^n$ analysis with n being equal to or greater than three, as will be described later.

For example, in the previously described case of FIG. 4, if a product ion having the mass-to-charge ratio of the product ion (d) or (e) has been found on the $MS^2$ spectrum, it is clear that the sugar-chain structure in question is not (c), but it is impossible to determine which of the remaining candidates (a) and (b) is the actual sugar-chain structure. Thus, in this example, although the number of sugar-chain structure candidates can be decreased, it is impossible to narrow down the candidates to one. By contrast, in the present embodiment, the sugar-chain structures can be further narrowed down by using an $MS^n$ analysis with n being equal to or greater than three.

Figure 7:
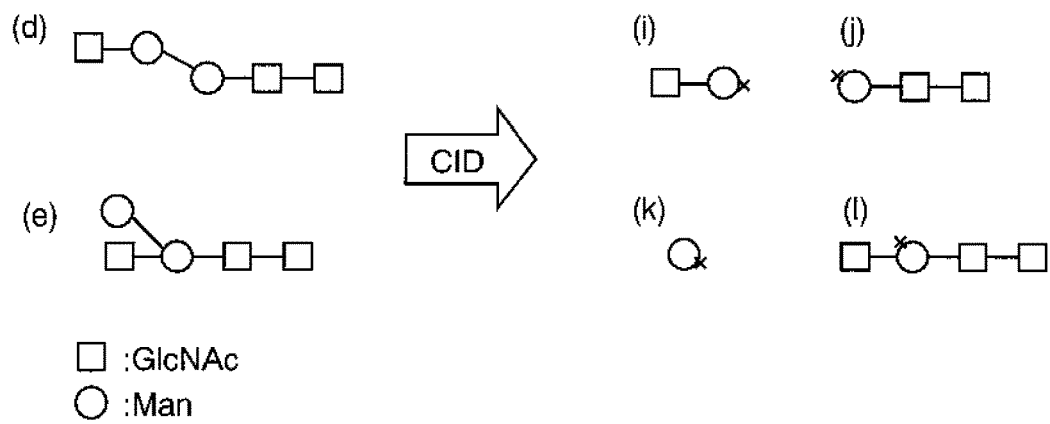
FIG. 7 is a model diagram showing a specific example of the procedure of deducing a sugar-chain structure according to the second embodiment.

FIG. 7 shows an example of narrowing down the candidates by using an $MS^3$ analysis in the case where a peak having the mass-to-charge ratio of the product ion (d) or (e) shown in FIG. 4 has been detected on the $MS^2$ spectrum. In FIG. 7, product ions (i) and (j) can only be obtained from the ion (d). That is to say, product ions which respectively have the same mass-to-charge ratios as the product ions (i) and (j) cannot be obtained by cutting any one bond in the sugar chain in the ion (e). On the other hand, product ions (k) and (l) can only be obtained from the ion (e).

Accordingly, if an actually measured $MS^3$ spectrum has a peak at the mass-to-charge ratio of the product ion (i) or (j), the precursor ion used in the $MS^3$ analysis should not be (e) but (d), so that the sugar-chain structure can be narrowed down to (a) (see FIG. 4). On the other hand, if the actually measured $MS^3$ spectrum has a peak at the mass-to-charge ratio of the product ion (k) or (l), the precursor ion used in the $MS^3$ analysis should not be (d) but (e), so that the sugar-chain structure can be narrowed down to (b).

Figure 8:
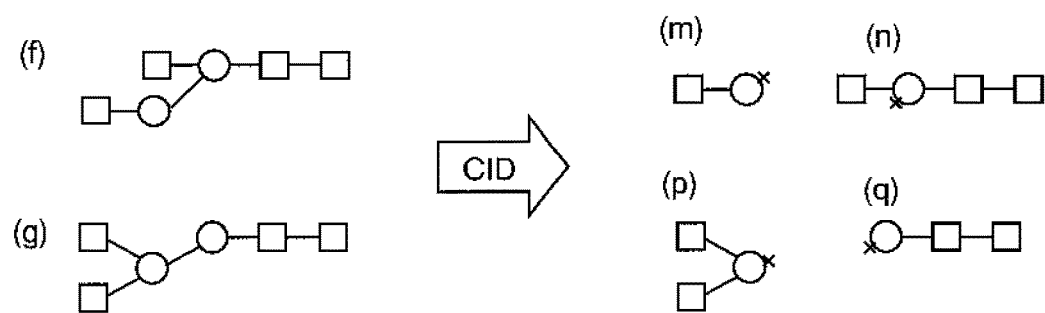
FIG. 8 is a model diagram showing another specific example of the procedure of deducing a sugar-chain structure according to the second embodiment.

FIG. 8 is an example of narrowing down the candidates by using an $MS^3$ analysis in the case where a peak having the mass-to-charge ratio of the product ion (f) or (g) shown in FIG. 4 has been detected on the $MS^2$ spectrum. In FIG. 8, product ions (m) and (n) can only be obtained from the ion (f). In other words, the product ions which respectively have the same mass-to-charge ratios as the product ions (m) and (n) cannot be obtained by cutting any one bond in the sugar chain in the ion (g). On the other hand, product ions (p) and (q) can only be obtained from the ion (g).

Accordingly, if an actually measured $MS^3$ spectrum has a peak at the mass-to-charge ratio of the product ion (m) or (n), the precursor ion used in the $MS^3$ analysis should not be (g) but (f), so that the sugar-chain structure can be narrowed down to (b). On the other hand, if the actually measured $MS^3$ spectrum has a peak at the mass-to-charge ratio of the product ion (p) or (q), the precursor ion used in the $MS^3$ analysis should not be (f) but (g), so that the sugar-chain structure can be narrowed down to (c).

In the sugar-chain structure analyzing system of the present embodiment, for example, when the sugar-chain structure candidates have been narrowed down to (a) and (b) by the candidate reliability judging processor 25, the precursor ion setter 27 orders the analysis control unit 3 to set, as the mass-to-charge ratio of the precursor ion, a mass-to-charge ratio of a product ion that is common to the remaining sugar-chain structure candidates. According to this order, an $MS^3$ analysis of a sample containing a test sugar chain is performed under the control of the analysis control unit 3, and an $MS^3$ spectrum data is stored in the spectrum data storage 21.

Meanwhile, the characteristic product ion calculator 24 calculates the mass-to-charge ratios of the product ions that can theoretically be generated in an $MS^3$ analysis for each of the product-ion structures (d) and (e) having the mass-to-charge ratios of the product ions common to the remaining sugar-chain structure candidates, and determines the mass-to-charge ratio of a characteristic product ion available for narrowing down the number of sugar-chain structure candidates. A specific procedure is as follows: As in the case of the $MS^2$ analysis, the mass-to-charge ratios of the product ions that will be generated by cutting any one sugar-chain bond (these ions correspond to the "secondary product ions" in the present invention) are calculated and listed, allowing a redundant occurrence of the same value. The lists are compared with the other to find, for each list, the mass-to-charge ratios of characteristic product ions which occur only in that list. The candidate reliability judging processor 25 retrieves the actually obtained $MS^3$ spectrum from the spectrum data storage 21, determines whether or not the $MS^3$ spectrum has a peak located at the mass-to-charge ratio of any of the aforementioned characteristic product ions, and based on the determination result, narrows down the number of sugar-chain structure candidates.

As described thus far, even if the sugar-chain structures cannot be narrowed down to one by using an $MS^2$ analysis, it is possible to narrow down the candidates by using an $MS^3$ analysis in which the sugar chain is further cut in another bond. An $MS^4$ analysis in which the sugar chain is further cut in yet another bond may also be used if the sugar-chain structures cannot be narrowed down to one candidate even by using the $MS^3$ analysis. In principle, there is no limitation on the value of n of the $MS^n$ analysis in the process of narrowing down the sugar-chain structures while increasing the value of n. However, it should be noted that increasing the value of n decreases the signal intensity. Practically, the upper limit of n is four or five.

In the case of the sugar-chain structure analyzing system of the first embodiment, since the analysis is performed only up to the $MS^2$ level, the mass spectrometer 1 does not need to have an ion trap 12 as shown in FIG. 1. For example, it is possible to use a mass spectrometer in which the CID operation of the ions is performed within a collision cell, as in a tandem quadrupole mass spectrometer.

The ion source 11 of the mass spectrometer 1 should preferably be a MALDI ion source, since this ion source produces a comparatively small amount of multiply charged ions. A presence of multiply charged ions makes the process complex since it is necessary to take into account the number of charges of an ion having a certain mass-to-charge ratio. Furthermore, it may possibly lead to a decrease in the accuracy of the structural deduction. Taking these factors into account, when an ion source which easily generates multiply charged ions (as in the case of an electrospray ion source) is used, it is preferable to identify the number of charges of each ion peak on an actually measured $MS^n$ spectrum and perform a process of extracting, for example, only the peaks of singly charged ions before detecting the peaks of characteristic product ions.

In the sugar-chain structure analyzing system of any of the previously described embodiments, if the structure of the test sugar chain can be determined in respect of its branching form, and if the sugar chain being analyzed is a sugar chain that is already registered in the database, it is possible to obtain information about the bonds other than the aforementioned branches, such as the location of a glycosidic bond between the simple sugars and its anomer (i.e. either α or β). Furthermore, even in the case where the sugar chain being analyzed is not registered in the database or such a database is not used in the first place, if the branching structure of the sugar chain is known, it is possible to more specifically determine the bonding location of carbons of simple sugars and anomer of the structure. In this case, information about which of the carbons in a simple sugar is engaged in the bonding should be obtained by another appropriate method, e.g. by once more performing the MS$^n$ analysis of the test sugar chain with an increased amount of CID energy and then detecting a characteristic product ion on the MS$^n$ spectrum for each of the possible bonding locations in a manner similar to the previously described embodiments.

It should be noted that the previously described embodiments are mere examples of the present invention, and any change, modification or addition appropriately made within the spirit of the present invention will naturally fall within the scope of claims of the present patent application.

EXPLANATION OF NUMERALS

1 ... Mass Spectrometer
11 ... MALDI Ion Source
12 ... Ion Trap
13 ... Time of Flight Mass Spectrometer
131 ... Flight Space
132 ... Detector
2 ... Analyzing and Processing Unit
21 ... Spectrum Data Storage
22 ... Sugar-Chain Structure Candidate Extractor
23 ... Sugar-Chain Database (DB)
24 ... Characteristic Product Ion Calculator
25 ... Candidate Reliability Judging Processor
26 ... Display Processor
27 ... Precursor Ion Setter
3 ... Analysis Control Unit
4 ... Display Unit

The invention claimed is:

1. A computational method for deducing a structure of a test sugar chain, comprising:
   a) an isomer candidate obtaining step, in which a plurality of isomer candidates of the test sugar chain is obtained based on a preliminarily determined mass-to-charge ratio of a precursor ion used in an MS$^2$ analysis of the test sugar chain;
   b) a characteristic ion obtaining step, in which product ions that can be generated by cutting a bond between sugars constituting the isomer candidates are theoretically calculated for each of the plurality of isomer candidates, and a product ion which appears only in one isomer candidate is extracted as a characteristic product ion from the calculated product ions for each of the isomer candidates; and
   c) a structure candidate judging step, in which a degree of reliability of each of the isomer candidates is judged based on a result of detection of a peak having a mass-to-charge ratio of the characteristic product ion in mass spectrum data obtained for the test sugar chain.

2. The method according to claim 1, wherein:
   in the isomer candidate obtaining step, the plurality of isomer candidates are calculated from the mass-to-charge ratio of the precursor ion used in the MS$^2$ analysis for the test sugar chain, using a database in which mass-to-charge ratios of precursor ions originating from sugar chains are stored, with each precursor ion related to a plurality of sugar-chain structures.

3. A computational method for deducing a structure of a test sugar chain, comprising:
   a) an isomer candidate obtaining step, in which a plurality of isomer candidates of the test sugar chain is obtained based on a preliminarily determined mass-to-charge ratio of a precursor ion used in an MS$^2$ analysis of the test sugar chain;
   b) a first characteristic ion obtaining step, in which product ions that can be generated by cutting a bond between sugars constituting the isomer candidates are calculated for each of the plurality of isomer candidates, and a product ion which appears only in one sugar chain candidate is extracted as a characteristic product ion from the calculated product ions for each of the isomer candidates;
   c) a characteristic ion detecting step, in which a peak having a mass-to-charge ratio of the characteristic product ion extracted in the first characteristic ion obtaining step or in a second characteristic ion obtaining step to be mentioned later is detected in MS$^m$ mass spectrum data (m is an integer greater than one) obtained for the test sugar chain;
   d) an MS$^{m+1}$ analyzing step, in which an MS$^{m+1}$ analysis of the test sugar chain is performed, where the mass-to-charge ratio of the characteristic product ion detected in the characteristic ion detecting step is set as the precursor ion;
   e) a second characteristic ion obtaining step, in which secondary product ions that can be generated by cutting a bond between sugars constituting a product ion having the mass-to-charge ratio of the precursor ion used in the MS$^{m+1}$ analysis is calculated, and a secondary product ion is extracted as a second characteristic product ion from the calculated secondary product ions for each of the characteristic product ions before dissociation; and
   f) a structure candidate judging step, in which a peak having a mass-to-charge ratio of the second characteristic product ion is detected in the MS$^{m+}$mass spectrum data obtained for the test sugar chain, a characteristic product ion before dissociation in a final stage of the MS$^{m+}$analysis is identified based on a result of the detection, and a degree of reliability of each of the plurality of isomer candidates is judged based on a result of the identification as well as a result of the peak detection in the characteristic ion detecting step,
   wherein, after the isomer candidate obtaining step and the first characteristic ion obtaining step are performed, the characteristic ion detecting step, the MS MS$^{m+}$analyzing step and the second characteristic ion obtaining step are performed one or more times while sequentially increasing the value of m from two, and subsequently, the structure candidate judging step is performed to narrow down the isomer candidates.

4. The method according to claim 3, wherein:
   in the isomer candidate obtaining step, the plurality of isomer candidates are calculated from the mass-to-charge ratio of the precursor ion used in the MS$^2$ analysis for the test sugar chain, using a database in which mass-to-charge ratios of precursor ions originating from sugar chains are stored, with each precursor ion related to a plurality of sugar-chain structures.

5. A system for deducing a structure of a test sugar chain, comprising a computer including a processor configured for:
   obtaining a plurality of isomer candidates of the test sugar chain, based on a preliminarily determined mass-to-charge ratio of a precursor ion used in an MS$^2$ analysis of the test sugar chain as an isomer candidate obtaining process,
   theoretically calculating product ions that can be generated by cutting a bond between sugars constituting each of the plurality of s isomer candidates, and extracting as a characteristic product ion a product ion which appears only in one isomer candidate from the calculated product ions for each of the isomer candidates as a characteristic ion obtaining process, and judging a degree of reliability of each of the isomer candidates based on a result of detection of a peak having a mass-to-charge ratio of the characteristic product ion in mass spectrum data obtained for the test sugar chain as a structure candidate judging process.

6. The system according to claim 5, further comprising:
a database in which mass-to-charge ratios of precursor ions originating from sugar chains are stored, with each precursor ion related to a plurality of sugar-chain structures,
wherein the plurality of isomer candidates are calculated from the mass-to-charge ratio of the precursor ion used in the $MS^2$ analysis for the test sugar chain.

7. A system for deducing a structure of a test sugar chain, comprising a computer including a processor configured for:
obtaining a plurality of isomer candidates of the test sugar chain, based on a preliminarily determined mass-to-charge ratio of a precursor ion used in an $MS^2$ analysis of the test sugar chain as a structure candidate obtaining process,
theoretically calculating product ions that can be generated by cutting a bond between sugars constituting the isomer candidates for each of the plurality of isomer candidates, and extracting a characteristic product ion from the calculated product ions for each of the sugar-chain structure candidates as a first characteristic ion obtaining process,
detecting, in an $MS^m$ spectrum (m is an integer greater than one and no greater than n) obtained for the test sugar chain, a peak having a mass-to-charge ratio of the characteristic product ion extracted in the first characteristic ion obtaining process or in a second characteristic ion obtaining process to be mentioned later as a characteristic ion detecting process,
performing an $MS^{m+}$ analysis where the mass-to-charge ratio of the characteristic product ion detected in the characteristic ion detecting process is set as the precursor ion as an $MS^{m+}$ analyzing process,
calculating secondary product ions that can be generated by cutting a bond between sugars constituting the characteristic product ion having the mass-to-charge ratio of the precursor ion used in the $MS^{m+}$ analysis, and extracting a secondary product ion as a second characteristic product ion from the calculated secondary product ions for each of the characteristic product ions before dissociation as a second characteristic ion obtaining process, and
detecting a peak having a mass-to-charge ratio of the second characteristic product ion in the $MS^{m+}$ mass spectrum data obtained for the test sugar chain, identifying a characteristic product ion before dissociation in a final stage of the $MS^{m+}$ analysis based on a result of the detection, and judging a degree of reliability of each of the plurality of isomer candidates based on a result of the identification as well as a result of the peak detection in the characteristic ion detecting process as a structure candidate judging process, wherein, after the structure candidate obtaining process and the first characteristic ion obtaining process, the characteristic ion detecting process, the $MS^{m+}$ analyzing process and the second characteristic ion obtaining process are performed one or more times while sequentially increasing the value of m from two, and subsequently, the structure candidate judging process is performed to narrow down the isomer candidates.

8. The system according to claim 7, further comprising:
a database in which mass-to-charge ratios of precursor ions originating from sugar chains are stored, with each precursor ion related to a plurality of sugar-chain structures,
wherein, in the structure candidate obtaining process, the plurality of isomer candidates are calculated from the mass-to-charge ratio of the precursor ion used in the $MS^2$ analysis for the test sugar chain.

9. A system for deducing a structure of a test sugar chain, comprising:
a mass spectrometer; and
a computer including a processor configured for
obtaining a plurality of isomer candidates of the test sugar chain, based on a preliminarily determined mass-to-charge ratio of a precursor ion used in an $MS^2$ analysis of the test sugar chain as a structure candidate obtaining process,
calculating product ions that can be generated by cutting a bond between sugars constituting each of the isomer candidates and extracting a product ion which appears in only one isomer candidate as a characteristic product ion from the calculated product ions for each of the isomer candidates as a characteristic ion obtaining process,
judging a degree of reliability of each of the isomer candidates based on a result of detection of a peak having a mass-to-charge ratio of the characteristic product ion in mass spectrum data obtained for the test sugar chain as a structure candidate judging process.

10. A system for deducing a structure of a test sugar chain, including:
a mass spectrometer: and
a computer including a processor configured for
obtaining a plurality of isomer candidates of the test sugar chain, based on a preliminarily determined mass-to-charge ratio of a precursor ion used in an $MS^2$ analysis of the test sugar chain as a structure candidate obtaining process,
theoretically calculating product ions that can be generated by cutting a bond between sugars constituting the isomer candidates for each of the plurality of isomer candidates, and extracting a product ion which appears in only one isomer candidate as a characteristic product ion from the calculated product ions for each of the isomer candidates as a first characteristic ion obtaining process,
detecting, in an $MS^m$ spectrum (m is an integer greater than one) obtained for the test sugar chain, a peak having a mass-to-charge ratio of the characteristic product ion extracted in the first characteristic ion obtaining process or in a second characteristic ion obtaining process to be mentioned later as a characteristic ion detecting process,
performing an $MS^{m+}$ analysis of the test sugar chain, where the mass-to-charge ratio of the characteristic product ion detected by the characteristic ion detecting process is set as the precursor ion as an $MS^{m+}$ analyzing process,
calculating secondary product ions that can be generated by dissociation of a characteristic product ion having the mass-to-charge ratio of the precursor ion used in the $MS^{m+}$ analysis, and extracting a characteristic secondary product ion as a second characteristic ion from the calculated secondary product ions for each of the characteristic product ions before dissociation as a second characteristic ion obtaining process, detecting a peak having a mass-to-charge ratio of the second characteristic product ion in the MS $^{m+}$spectrum obtained for the test sugar chain, for identifying a characteristic product ion before dissociation in a final stage of the MS $^{m+}$analysis based on a result of the detection, and judging a degree of reliability of each of the plurality of isomer candidates based on a result of the identification as well as a result of the peak detection in the characteristic ion detecting process as a structure candidate judging process, wherein, after the structure candidate obtaining process and the first characteristic ion obtaining process, the characteristic ion detecting process, the MS $^{m+}$analyzing process and the second characteristic ion obtaining process are performed one or more times while sequentially increasing the value of m from two, and subsequently, the structure candidate judging process is performed to narrow down the sugar-chain structure candidates.

* * * * *